United States Patent
Almansa Rosales et al.

(10) Patent No.: US 6,743,816 B2
(45) Date of Patent: Jun. 1, 2004

(54) IMIDAZOLE DERIVATIVES WITH ANTI-INFLAMMATORY ACTIVITY

(75) Inventors: Carmen Almansa Rosales, Barcelona (ES); Concepción González González, Barcelona (ES); María Carmen Torres Barreda, Badalona (ES)

(73) Assignee: J. Uriach & Cia S.A., Barcelona (ES)

( * ) Notice: Subject to any disclaimer, the term of this patent is extended or adjusted under 35 U.S.C. 154(b) by 0 days.

(21) Appl. No.: 10/239,359

(22) PCT Filed: Mar. 22, 2001

(86) PCT No.: PCT/ES01/00114
§ 371 (c)(1),
(2), (4) Date: Jan. 9, 2003

(87) PCT Pub. No.: WO01/70704
PCT Pub. Date: Sep. 27, 2001

(65) Prior Publication Data
US 2003/0176481 A1 Sep. 18, 2003

(30) Foreign Application Priority Data
Mar. 23, 2000 (ES) .............................. 200000707

(51) Int. Cl.⁷ ................ A61K 31/4164; A61K 31/4178; C07D 233/68; C07D 405/04
(52) U.S. Cl. .................... 514/397; 514/396; 548/311.7; 548/343.1
(58) Field of Search ............... 548/311.7, 343.1; 514/396, 397

(56) References Cited

U.S. PATENT DOCUMENTS 3,901,908 A   8/1975   Fitzi et al.

FOREIGN PATENT DOCUMENTS

| EP | 0 074 130 A2 | 3/1983 |
| EP | 1 122 243 A1 | 8/2001 |
| WO | WO 96/03387 A1 | 2/1996 |
| WO | WO 96/03388 A1 | 2/1996 |

OTHER PUBLICATIONS

Khanna, Ish K. et al., "1,2–Diarylimidazoles as Potent, Cyclooxygenase–2 Selective, and Orally Active Antiinflammatory Agents," *J. Med. Chem.*, 1997, vol. 49, 1634–1647. American Chemical Society.

Primary Examiner—Laura L. Stockton
(74) Attorney, Agent, or Firm—Rothwell, Figg, Ernst & Manbeck

(57) ABSTRACT

Novel imidazole derivatives of formula I and their salts, solvates and prodrugs, wherein the meanings of the different radicals are as shown in the description. Said compounds are useful as anti-inflammatory agents.

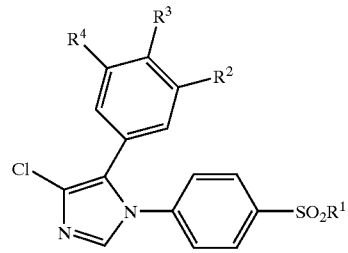

30 Claims, No Drawings

IMIDAZOLE DERIVATIVES WITH ANTI-INFLAMMATORY ACTIVITY

FIELD OF THE INVENTION

The present invention relates to a new series of imidazole derivatives with anti-inflammatory activity, as well as to a process for their preparation, to the pharmaceutical compositions containing them and to their use in medicine.

DESCRIPTION OF THE PRIOR ART

In many acute as well as chronic inflammatory processes, substances derived from the metabolism of arachidonic acid are involved. These substances form a large family of compounds of lipidic nature that are the result of the action of a series of enzymes which form what is called the arachidonic acid cascade. The most important one from the therapeutic point of view is prostaglandin G/H synthase (PGHS), also known as cyclooxygenase (COX), which catalyzes the formation of vasoactive and inflammatory substances such as prostaglandins ($PGE_2$, $PGD_2$, $PGF_2$), prostacyclin ($PGI_2$) and thromboxane $A_2$ ($TXA_2$).

Inhibition of cyclooxygenase (COX) is the mechanism of action responsible for the effect of most anti-inflammatory drugs on the market (non-steroidal anti-inflammatory drugs, NSAIDs). Said inhibition also reduces the levels of prostaglandins at gastric level, which, in view of the protective role of said molecules on the gastric mucosa, has been correlated to the well known gastric effects of NSAIDs.

In the early 90's two cyclooxygenase isoforms, COX-1 and COX-2, were described. COX-1 is the constitutive isoform, present in many tissues, but preferentially in the stomach, kidney and platelets. Its inhibition is responsible for the gastric and renal effects of NSAIDs. On the other hand, COX-2 is an inducible isoform, which is expressed as a consequence of an inflammatory or mitogenic stimulus in a wide range of tissues such as macrophages, chondrocytes, fibroblasts and endothelial cells.

The discovery of the inducible isoenzyme of PGHS ($PGHS_2$ or COX-2) has allowed the synthesis of selective COX-2 inhibitors which presumably improve the gastric tolerance of these drugs, since as they inhibit the constitutive form present in the stomach to a lesser extent, they exhibit reduced ulcerogenic potency (one of the most characteristic side effects of non-selective inhibitors). The present invention describes new cyclooxygenase inhibitors with selectivity for the isoform 2 (COX-2).

DESCRIPTION OF THE INVENTION

The present invention relates to the new compounds of general formula I

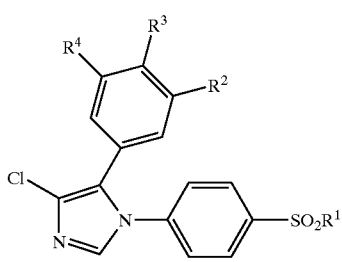

I wherein $R^1$, $R^2$, $R^3$ and $R^4$ represent the specific combinations of values defined in the following table:

| $R^1$ | $R^2$ | $R^3$ | $R^4$ |
|---|---|---|---|
| —$CH_3$ | —H | —$OCH(CH_3)_2$ | —H |
| —$CH_3$ | —$OCH_3$ | —F | —H |
| —$CH_3$ | —F | —$OCH_2CH_3$ | —H |
| —$CH_3$ | —F | —H | —F |
| —$CH_3$ | —Cl | —$OCH_3$ | —H |
| —$CH_3$ | —Cl | —$OCH_2CH_3$ | —H |
| —$CH_3$ | —$OCH_2O$— | | —H |
| —$CH_3$ | —Cl | —$OCH_3$ | —Cl |
| —$CH_3$ | —H | —$CH(CH_3)_2$ | —H |
| —$CH_3$ | —H | —$N(CH_2CH_3)_2$ | —H |
| —$NH_2$ | —$OCH_3$ | —F | —H |
| —$NH_2$ | —F | —$OCH_2CH_3$ | —H |
| —$NH_2$ | —Cl | —$OCH_2CH_3$ | —H |
| —$NH_2$ | —Cl | —$OCH_3$ | —H |
| —$NH_2$ | —Cl | —$OCH_3$ | —Cl |
| —$CH_3$ | —H | —$CH_2CH_2CH_3$ | —H |

The present invention also relates to the addition salts of the compounds of the invention as well as to their solvates and prodrugs. The term prodrug refers to any precursor of a compound of formula I which is able to be transformed in vivo into a compound of formula I.

The present invention also relates to the pharmaceutical compositions which comprise an effective amount of a compound of formula I or a pharmaceutically acceptable salt, solvate or prodrug thereof and one or more pharmaceutically acceptable excipients.

The present invention also relates to the use of a compound of formula I or a pharmaceutically acceptable salt, solvate or prodrug thereof for the manufacture of a medicament for the treatment or prevention of diseases mediated by cyclooxygenase, specially cyclooxygenase-2.

The present invention also relates to the use of a compound of formula I or a pharmaceutically acceptable salt, solvate or prodrug thereof for the manufacture of a medicament for the treatment of inflammation, pain and/or fever.

The present invention also relates to the use of a compound of formula I or a pharmaceutically acceptable salt, solvate or prodrug thereof for the manufacture of a medicament for inhibiting prostanoid-induced smooth muscle contraction.

The present invention also relates to the use of a compound of formula I or a pharmaceutically acceptable salt, solvate or prodrug thereof for the manufacture of a medicament for the treatment or prevention of dysmenorrhea, preterm labour, asthma and bronchitis.

The present invention also relates to the use of a compound of formula I or a pharmaceutically acceptable salt, solvate or prodrug thereof for the manufacture of a medicament for the treatment or prevention of familial adenomatous polyposis.

The present invention also relates to the use of a compound of formula I or a pharmaceutically acceptable salt, solvate or prodrug thereof for the manufacture of a medicament for the treatment or prevention of cancer, preferably gastrointestinal cancers, and more preferably colon cancer.

The present invention also relates to the use of a compound of formula I or a pharmaceutically acceptable salt, solvate or prodrug thereof for the manufacture of a medicament for the treatment or prevention of cerebral infarction, epilepsy, and neurodegenerative diseases such as Alzheimer's disease and dementia.

The present invention also relates to a compound of formula I or a pharmaceutically acceptable salt, solvate or prodrug thereof for the treatment or prevention of diseases mediated by cyclooxygenase, specially cyclooxygenase-2.

The present invention also relates to a compound of formula I or a pharmaceutically acceptable salt, solvate or prodrug thereof for the treatment of inflammation, pain and/or fever.

The present invention also relates to a compound of formula I or a pharmaceutically acceptable salt, solvate or prodrug thereof for inhibiting prostanoid-induced smooth muscle contraction.

The present invention also relates to a compound of formula I or a pharmaceutically acceptable salt, solvate or prodrug thereof for the treatment or prevention of dysmenorrhea, preterm labour, asthma and bronchitis.

The present invention also relates to a compound of formula I or a pharmaceutically acceptable salt, solvate or prodrug thereof for the treatment or prevention of familial adenomatous polyposis.

The present invention also relates to a compound of formula I or a pharmaceutically acceptable salt, solvate or prodrug thereof for the treatment or prevention of cancer, preferably gastrointestinal cancers, and more preferably colon cancer.

The present invention also relates to a compound of formula I or a pharmaceutically acceptable salt, solvate or prodrug thereof for the treatment or prevention of cerebral infarction, epilepsy, and neurodegenerative diseases such as Alzheimer's disease and dementia.

The present invention also relates to the use of a compound of formula I or a pharmaceutically acceptable salt, solvate or prodrug thereof for the treatment or prevention of diseases mediated by cyclooxygenase, specially cyclooxygenase-2.

The present invention also relates to the use of a compound of formula I or a pharmaceutically acceptable salt, solvate or prodrug thereof for the treatment of inflammation, pain and/or fever.

The present invention also relates to the use of a compound of formula I or a pharmaceutically acceptable salt, solvate or prodrug thereof for inhibiting prostanoid-induced smooth muscle contraction.

The present invention also relates to the use of a compound of formula I or a pharmaceutically acceptable salt, solvate or prodrug thereof for the treatment or prevention of dysmenorrhea, preterm labour, asthma and bronchitis.

The present invention also relates to the use of a compound of formula I or a pharmaceutically acceptable salt, solvate or prodrug thereof for the treatment or prevention of familial adenomatous polyposis.

The present invention also relates to the use of a compound of formula I or a pharmaceutically acceptable salt, solvate or prodrug thereof for the treatment or prevention of cancer, preferably gastrointestinal cancers, and more preferably colon cancer.

The present invention also relates to the use of a compound of formula I or a pharmaceutically acceptable salt, solvate or prodrug thereof for the treatment or prevention of cerebral infarction, epilepsy, and neurodegenerative diseases such as Alzheimer's disease and dementia.

The present invention also relates to a method of treating or preventing diseases mediated by cyclooxygenase, specially cyclooxygenase-2, in a mammal in need thereof, specially a human being, which comprises administering to said mammal a therapeutically effective amount of a compound of formula I or a pharmaceutically acceptable salt, solvate or prodrug thereof.

The present invention also relates to a method of treating inflammation, pain and/or fever in a mammal in need thereof, specially a human being, which comprises administering to said mammal a therapeutically effective amount of a compound of formula I or a pharmaceutically acceptable salt, solvate or prodrug thereof.

The present invention also relates to a method of inhibiting prostanoid-induced smooth muscle contraction in a mammal in need thereof, specially a human being, which comprises administering to said mammal a therapeutically effective amount of a compound of formula I or a pharmaceutically acceptable salt, solvate or prodrug thereof.

The present invention also relates to a method of treating or preventing dysmenorrhea, preterm labour, asthma and bronchitis in a mammal in need thereof, specially a human being, which comprises administering to said mammal a therapeutically effective amount of a compound of formula I or a pharmaceutically acceptable salt, solvate or prodrug thereof.

The present invention also relates to a method of treating or preventing familial adenomatous polyposis in a mammal in need thereof, specially a human being, which comprises administering to said mammal a therapeutically effective amount of a compound of formula I or a pharmaceutically acceptable salt, solvate or prodrug thereof.

The present invention also relates to a method of treating or preventing cancer, preferably gastrointestinal cancers, and more preferably colon cancer, in a mammal in need thereof, specially a human being, which comprises administering to said mammal a therapeutically effective amount of a compound of formula I or a pharmaceutically acceptable salt, solvate or prodrug thereof.

The present invention also relates to a method of treating or preventing cerebral infarction, epilepsy, and neurodegenerative diseases such as Alzheimer's disease and dementia in a mammal in need thereof, specially a human being, which comprises administering to said mammal a therapeutically effective amount of a compound of formula I or a pharmaceutically acceptable salt, solvate or prodrug thereof.

Another object of the present invention is to provide a process for preparing the compounds of formula I, which comprises:

a) reacting a compound of formula II

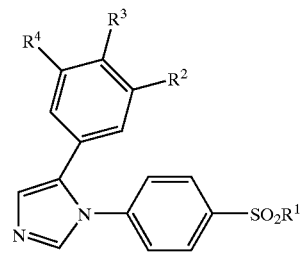

II wherein $R^1$, $R^2$, $R^3$ and $R^4$ have the meaning described above, with a chlorinating agent; or b) when in a compound of formula I $R^1$ represents —$CH_3$, reacting a compound of formula VI

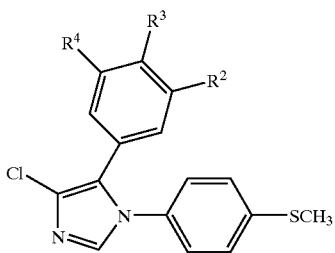

wherein R², R³ and R⁴ have the meaning described above, with an oxidizing agent; or c) when in a compound of formula I R¹ represents —NH₂, reacting a compound of formula VII

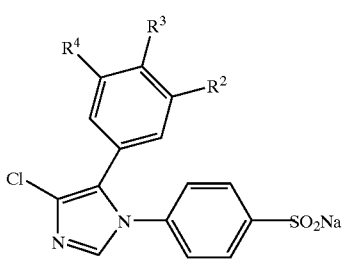

wherein R², R³ and R⁴ have the meaning described above, with hydroxylamine-O-sulfonic acid; or d) if desired, after the above steps, reacting a compound of formula I with an acid or a base to give the corresponding salt.

In a preferred embodiment of the invention, the compound of formula I is 4-chloro-5-(4-isopropoxyphenyl)-1-(4-methylsulfonylphenyl)imidazole or a salt, solvate or prodrug thereof.

In another preferred embodiment of the invention, the compound of formula I is 4-chloro-5-(4-fluoro-3-methoxyphenyl)-1-(4-methylsulfonylphenyl)imidazole or a salt, solvate or prodrug thereof.

In another preferred embodiment of the invention, the compound of formula I is 4-chloro-5-(4-ethoxy-3-fluorophenyl)-1-(4-methylsulfonylphenyl)imidazole or a salt, solvate or prodrug thereof.

In another preferred embodiment of the invention, the compound of formula I is 4-chloro-5-(3,5-difluorophenyl)-1-(4-methylsulfonylphenyl)imidazole or a salt, solvate or prodrug thereof.

In another preferred embodiment of the invention, the compound of formula I is 4-chloro-5-(3-chloro-4-methoxyphenyl)-1-(4-methylsulfonylphenyl)imidazole or a salt, solvate or prodrug thereof.

In another preferred embodiment of the invention, the compound of formula I is 4-chloro-5-(3-chloro-4-ethoxyphenyl)-1-(4-methylsulfonylphenyl)imidazole or a salt, solvate or prodrug thereof.

In another preferred embodiment of the invention, the compound of formula I is 4-chloro-5-[3,4-(methylenedioxy)phenyl]-1-(4-methylsulfonylphenyl)imidazole or a salt, solvate or prodrug thereof.

In another preferred embodiment of the invention, the compound of formula I is 4-chloro-5-(3,5-dichloro-4-methoxyphenyl)-1-(4-methylsulfonylphenyl)imidazole or a salt, solvate or prodrug thereof.

In another preferred embodiment of the invention, the compound of formula I is 4-chloro-5-(4-isopropylphenyl)-1-(4-methylsulfonylphenyl)imidazole or a salt, solvate or prodrug thereof.

In another preferred embodiment of the invention, the compound of formula I is 4-chloro-5-(4-N,N-diethylaminophenyl)-1-(4-methylsulfonylphenyl)imidazole or a salt, solvate or prodrug thereof.

In another preferred embodiment of the invention, the compound of formula I is 4-[4-chloro-5-(4-fluoro-3-methoxyphenyl)imidazol-1-yl]benzenesulfonamide or a salt, solvate or prodrug thereof.

In another preferred embodiment of the invention, the compound of formula I is 4-[4-chloro-5-(4-ethoxy-3-fluorophenyl)imidazol-1-yl]benzenesulfonamide or a salt, solvate or prodrug thereof.

In another preferred embodiment of the invention, the compound of formula I is 4-[4-chloro-5-(3-chloro-4-ethoxyphenyl)imidazol-1-yl]benzenesulfonamide or a salt, solvate or prodrug thereof.

In another preferred embodiment of the invention, the compound of formula I is 4-[4-chloro-5-(3-chloro-4-methoxyphenyl)imidazol-1-yl]benzenesulfonamide or a salt, solvate or prodrug thereof.

In another preferred embodiment of the invention, the compound of formula I is 4-[4-chloro-5-(3,5-dichloro-4-methoxyphenyl)imidazol-1-yl]benzenesulfonamide or a salt, solvate or prodrug thereof.

In another preferred embodiment of the invention, the compound of formula I is 4-chloro-1-(4-methylsulfonylphenyl)-5-(4-propylphenyl)imidazole or a salt, solvate or prodrug thereof.

The compounds of the present invention contain one or more basic nitrogens and, consequently, they can form salts with organic as well as inorganic acids, which are also included in the present invention. Examples of said salts include salts with inorganic acids such as hydrochloric acid, hydrobromic acid, hydroiodic acid, nitric acid, perchloric acid, sulfuric acid or phosphoric acid; and salts with organic acids, such as methanesulfonic acid, trifluoromethanesulfonic acid, ethanesulfonic acid, benzenesulfonic acid, p-toluenesulfonic acid, fumaric acid, oxalic acid, acetic acid or maleic acid, among others. The compounds of formula I where R¹=NH₂ can also form salts with bases, which are also included in the present invention; examples thereof include salts with inorganic cations such as sodium, potassium, calcium, magnesium, lithium, aluminum, zinc, etc. There is no limitation on the nature of said salts, provided that, when used for therapeutic purposes they are pharmaceutically acceptable. The salts can be prepared by treatment of a compound of formula I with a sufficient amount of the desired acid or base to give the salt in a conventional manner. The compounds of formula I and their salts differ in certain physical properties, such as solubility, but they are equivalent for the purposes of the invention.

Some compounds of the present invention may exist in solvated form, including hydrated forms. In general, the solvated forms, with pharmaceutically acceptable solvents such as water, ethanol and the like, are equivalent to the unsolvated form for the purposes of the invention.

The present invention also provides a process for the preparation of the compounds of formula I. As it will be obvious to a person skilled in the art, the precise method used for the preparation of a given compound can vary depending on its chemical structure. Furthermore, in some of the processes that are detailed below it may be necessary or appropriate to protect the reactive or labile groups using conventional protecting groups. Both the nature of said protecting groups and the processes for their introduction and removal are well known and belong to the state of the art (see for example Greene T. W., "Protective Groups in Organic Synthesis", John Wiley & Sons, New York, 1981).

The compounds of formula I are in general obtained by reacting a compound of formula II with a suitable chlorinating agent such as N-chlorosuccinimide, as shown in the following scheme:

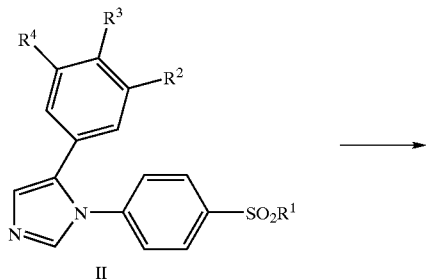

II

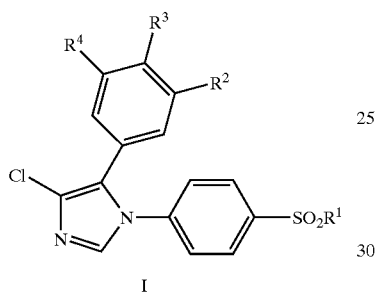

I wherein $R^1$, $R^2$, $R^3$ and $R^4$ have the meaning described above. This reaction is carried out in a suitable solvent such as acetonitrile, and heating, preferably at reflux.

The compounds of formula II can in general be obtained by reacting an imine of formula III

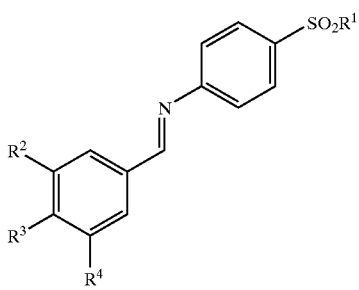

III with an isocyanide of formula L—CH$_2$—NC (wherein L is a good leaving group) such as tosylmethylisocyanide or 1H-benzotriazol-1-ylmethylisocyanide, in the presence of a base such as K$_2$CO$_3$, in a suitable solvent such as methanol-dimethoxyethane mixtures, and heating, preferably at reflux.

The imines of formula III can be prepared by condensation of an aldehyde of formula IV

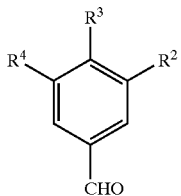

IV wherein $R^2$, $R^3$ and $R^4$ have the meaning described above, with an amine of formula $R^1SO_2$—$C_6H_4$—$NH_2$ (V), and heating at reflux in a suitable solvent such as toluene, in a Dean Stark. The compounds of formula IV and V are commercially available or can be prepared according to procedures well known by those skilled in the art, such as for example those described in the examples.

Alternatively, a compound of formula I or II wherein $R^1$ represents a group —CH$_3$ and $R^2$, $R^3$ and $R^4$ have the meaning described above, can also be prepared from the corresponding thioether of formula VI or VI', respectively

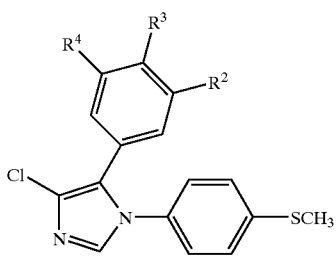

VI

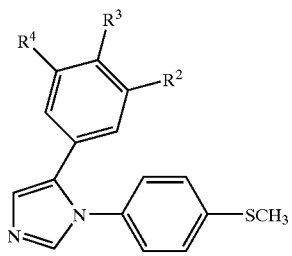

VI' wherein $R^2$, $R^3$ and $R^4$ have the meaning described above, by oxidation with a suitable oxidizing agent such as m-chloroperbenzoic acid, magnesium monoperoxyphtalate or Oxone®, in a suitable solvent such as a halogenated hydrocarbon, for example dichloromethane.

Alternatively, the compounds of formula I wherein $R^1$ represents a group —NH$_2$ can also be prepared from the corresponding sodium sulfinate of formula VII

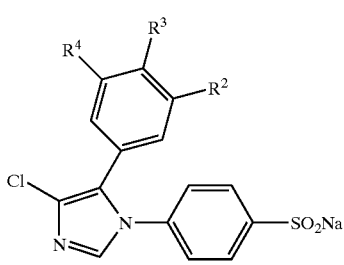

VII wherein R², R³ and R⁴ have the meaning described above, by reaction with hydroxylamine-O-sulfonic acid in a suitable solvent such as water or water/tetrahydrofuran mixtures.

The compounds of formula VII are prepared from the methylsulfoxide of formula VIII,

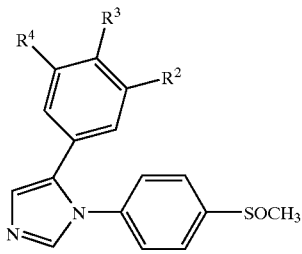

VIII wherein R², R³ and R⁴ have the meaning described above, by a process that involves treatment with acetic anhydride to give the corresponding acetoxymethylthio derivative (—SCH₂OAc), followed by chlorination of the position 4 of the imidazole ring using the general procedure described above for the preparation of the compounds of formula I and finally oxidation of the group —SCH₂OAc with a suitable oxidizing agent such as magnesium monoperoxyphtalate to give the —SO₂CH₂OAc derivative, which is transformed into a sodium sulfinate of formula VII by treatment with a base, for example sodium hydroxide.

The compounds of formula VIII and VI' can be prepared using the same general method described above for preparing the compounds of formula II but starting from compounds of formula III which contain a group —SOCH₃ or —SCH₃, respectively, instead of —SO₂CH₃. The compounds of formula VI can be prepared from the corresponding compound VI' by chlorination, according to the method previously described. The derivatives VIII can also be prepared from a compound of formula VI', by oxidation with a suitable oxidizing agent.

The salts of the compounds of formula I can be prepared by conventional methods by treatment for example with an acid such as hydrochloric acid, sulfuric acid, nitric acid, oxalic acid or methanesulfonic acid or with a base such as sodium or potassium hydroxide.

As mentioned above, the compounds of the present invention act by inhibiting the cyclooxygenase-2 enzyme (COX-2). Therefore, they are useful for the treatment or prevention of inflammation, pain and/or fever associated with a wide range of diseases or pathologies, which include among others: rheumatic fever; symptoms associated with influenza or other viral infections; common cold; low back and neck pain; dysmenorrhea; headache; toothache; myositis; neuralgia; synovitis; bursitis; arthritis, including rheumatoid arthritis and juvenile arthritis; degenerative joint diseases, including osteoarthritis; gout and ankylosing spondylitis; lupus erythematosus; tendinitis; sprains, strains and other similar injuries, such as those produced during sport performance; pain following surgical or dental procedures; and pain associated with cancer. They are also useful in the treatment of skin inflammatory diseases, including psoriasis, eczema, burns and dermatitis.

The compounds of the present invention can also be useful for the treatment of other pathologies mediated by COX-2. For example, the compounds of formula I can inhibit cell proliferation and consequently they can be useful for the treatment or prevention of familial adenomatous polyposis and cancer, specially those cancers that produce prostaglandins or that express cyclooxygenase. The compounds of the invention are useful for the treatment, for example, of liver, bladder, pancreas, ovary, prostate, cervix, lung, breast and skin cancer, and specially gastrointestinal cancers such as colon cancer.

The compounds of the present invention can also inhibit prostanoid-induced smooth muscle contraction and thus can be useful for the treatment of dysmenorrhea, preterm labour, asthma and bronchitis. Other uses of the compounds of formula I include the treatment or prevention of cerebral infarction, epilepsy, and neurodegenerative diseases, such as Alzheimer's disease and dementia.

Likewise, the compounds of the present invention can be used for treating inflammation in diseases such as vascular diseases, migraine, periarteritis nodosa, thyroiditis, aplastic anaemia, Hodgkin's disease, scleroderma, type I diabetes, myasthenia gravis, sarcoidosis, nephrotic syndrome, Behcet's syndrome, polymyositis, hypersensitivity, conjunctivitis, gingivitis and myocardial ischaemia.

Due to their selectivity for cyclooxygenase-2, the compounds of the present invention are useful as an alternative to non-steroidal anti-inflammatory drugs (NSAIDs), specially in those cases in which NSAIDs may be contraindicated.

According to the activity of the products herein described, the present invention also relates to compositions which comprise a compound of the present invention, together with an excipient or other auxiliary agents if necessary. The compounds of the present invention can be administered as any pharmaceutical formulation, the nature of which will depend, as it is well known, upon the route of administration and upon the nature of the pathology to be treated.

According to the present invention, solid compositions for oral administration include tablets, powders for extemporaneous suspensions, granulates and capsules. In tablets, the active component is admixed with at least one inert diluent such as lactose, starch, mannitol, microcrystalline cellulose or calcium phosphate; with a binding agent such as for example starch, gelatin, microcrystalline cellulose or polyvinylpyrrolidone; and with a lubricating agent, such as for example magnesium stearate, stearic acid or talc. The tablets can be coated by known techniques with the purpose of delaying their disintegration and absorption in the gastrointestinal tract, and thereby provide a sustained action over a longer period. Gastric or enteric coatings can be made with sugar, gelatin, hydroxypropylcellulose, acrylic resins, etc. Sustained-release tablets might also be obtained using an excipient which produces regressive osmosis, such as galacturonic acid polymers. Preparations for oral use can also be presented as hard capsules of absorbable material, such as for example gelatin, wherein the active compound is mixed with an inert solid diluent and lubricating agents, or pasty materials, such as ethoxylated saturated glycerides, which might also provide controlled release. Soft gelatin capsules are also possible, wherein the active compound is mixed with water or an oily medium, for example coconut oil, liquid paraffin, or olive oil.

Powders and granulates for the preparation of suspensions by the addition of water can be obtained by mixing the active compound with dispersing or wetting agents; suspending agents, such as sodium carboxymethylcellulose, methylcellulose, hydroxypropylmethylcellulose, sodium alginate, polyvinylpyrrolidine, gum tragacanth, xantham gum, gum acacia, and one or more preservatives, such as methyl or propyl p-hydroxybenzoate. Other excipients can also be added, for example sweetening, flavouring and colouring agents.

Liquid forms for oral administration include emulsions, solutions, suspensions, syrups and elixirs containing commonly used inert diluents, such as distilled water, ethanol, sorbitol, glycerol or propylene glycols. Said compositions can also contain coadjuvants such as wetting, suspending, sweetening, flavouring, preserving agents and buffers.

Injectable preparations, according to the present invention, for parenteral administration comprise sterile aqueous or non-aqueous solutions, suspensions or emulsions, in a suitable non-toxic solvent or diluent. Examples of aqueous solvents or suspending media are distilled water for injection, Ringer's solution and isotonic sodium chloride solution. As non-aqueous solvents or suspending media propylene glycol, polyethylene glycol, vegetable oils such as olive oil, or alcohols such as ethanol can be used. These compositions can also contain coadjuvants, such as wetting, preserving, emulsifying and dispersing agents. They may be sterilized by any known method or prepared as sterile solid compositions which will be dissolved in water or any other sterile injectable medium immediately before use. It is also possible to start from sterile materials and keep them under these conditions throughout all the manufacturing process.

The dosage and frequency of doses will depend upon the nature and severity of the disease to be treated, the age and body weight of the patient, as well as the route of administration. In general, the daily dose for an adult will be comprised between 1 and 1000 mg per day, which can be administered as a single or divided doses. However, in special cases, doses outside these margins might be necessary. A person skilled in the art will be able to easily determine the suitable dose for each situation.

Some examples of representative formulations for tablets, capsules and injectable preparations are cited below. They can be prepared by conventional procedures and are useful for inhibiting cyclooxygenase-2.

| Tablets | |
|---|---|
| Compound of formula I | 100 mg |
| Dibasic calcium phosphate | 125 mg |
| Sodium starch glycolate | 10 mg |
| Talc | 12.5 mg |
| Magnesium stearate | 2.5 mg |
| | 250.0 mg |
| Hard gelatin capsules | |
| Compound of formula I | 100 mg |
| Lactose | 197 mg |
| Magnesium stearate | 3 mg |
| | 300 mg |
| Injectable | |
| Compound of formula I | 100 mg |
| Benzylic alcohol | 0.05 mL |
| Propylene glycol | 1 mL |
| Water to | 5 mL |

The activity of the compounds of the present invention can be determined using the following test:

Inhibition of Cyclooxygenase-1 (COX-1) and Cyclooxygenase-2 (COX-2) Activity in Human Cell Lines The inhibition of COX-1 and COX-2 is determined by assessing the $PGE_2$ production after stimulation with arachidonic acid in cell lines expressing human COX-1 (U-937 from human histiocitic lymphoma) and human COX-2 (143.98.2 from human osteosarcoma), respectively.

The osteosarcoma-derived cells were cultured in 1 mL of DMEM culture medium supplemented with 10% fetal calf serum, in 24-well multidishes until confluence. U-937 cells were cultured in RPMI medium supplemented with 10% fetal calf serum in flasks.

To evaluate COX-2 activity, the medium was removed and replaced with Hepes-buffered saline solution (HBSS) without $Ca^{2+}/Mg^{2+}$ ($2 \times 10^5$ cells/well). To evaluate COX-1 activity, the medium was removed and U-937 cells were resuspended to a final density of $3 \times 10^6$ cells/mL in HBSS without $Ca^{2+}/Mg^{2+}$ (1 mL/well, in 24-well multidishes). 1 $\mu$L of a solution of the test compound dissolved in DMSO or vehicle was added, and the samples were incubated for 15 min at 37° C. (5% $CO_2$ and 95% humidity). Arachidonic acid was added (final concentration: 10 $\mu$M) and the samples were incubated for 10 min more. Next the reactions were quenched by adding indomethacin (8 mM, 30 $\mu$L). The amount of $PGE_2$ in the supernatant was determined by specific enzymatic immunoassay (Kit Prostaglandin E2, Biotrak EIA system RPN222, Amersham Pharmacia Biotech). All the assays were performed in triplicate.

The results obtained with the compounds of the present invention are shown in the following table, where the % of inhibition of COX-1 and COX-2 activity at a concentration of 0.1 $\mu$M of test compound are reported.

| | % Inhibition (0.1 $\mu$M) | |
|---|---|---|
| Example | COX-1 | COX-2 |
| 1 | 0 | 52 |
| 2 | 0 | 82 |
| 3 | 15 | 76 |
| 4 | 2 | 57 |
| 5 | 17 | 92 |
| 6 | 0 | 87 |
| 7 | 1 | 98 |
| 8 | 0 | 92 |
| 9 | 0 | 82 |
| 10 | 0 | 64 |
| 11 | 0 | 88 |
| 12 | 0 | 65 |
| 13 | 0 | 97 |
| 14 | 8 | 87 |
| 15 | 0 | 90 |
| 16 | 0 | 48 |

The results of the table above show that the compounds of formula I are potent and selective COX-2 inhibitors.

The following examples illustrate, but do not limit, the scope of the present invention. The following abbreviations have been used in the examples:

EtOAc: ethyl acetate
$Ac_2O$: acetic anhydride
NaOAc: sodium acetate
DME: dimethoxyethane
DMF: dimethylformamide
DMSO: dimethylsulfoxide
EtOH: ethanol
$Et_2O$: diethyl ether
MeOH: methanol
$Et_3N$: triethylamine
THF: tetrahydrofuran
TMS: tetramethylsilane Reference Example 1

4-Methylsulfonylaniline 67 mg of $Na_2WO_4$, 8 drops of acetic acid and 19 mL of $H_2O$ were introduced into a flask and heated to 65° C. Then, 19 mL (153 mmol) of 4-methylthioaniline was added followed by the dropwise addition of 34.5 mL (337 mmol) of $H_2O_2$. The mixture was stirred at 65° C. for 1.5 h and, after cooling, 800 mL of 1N HC and 500 mL of $CHCl_3$ was added. The layers were separated and the aqueous phase was washed with more $CHCl_3$. The aqueous phase was then basified with 25% NaOH and extracted with $CHCl_3$. The organic phase was washed with brine and dried over $MgSO_4$. The solvent was removed, yielding 19.80 g of the product as a white solid (75% yield).

$^1$H-NMR (300 MHz, $CDCl_3$ δ TMS): 2.97 (s, 3 H), 4.04 (s, 2 H), 6.66 (d, J=9 Hz, 2 H), 7.56 (d, J=9 Hz, 2 H).

Reference Example 2

4-Methylsulfinylaniline 20 g (143.66 mmol) of 4-methylthioaniline was placed in a flask and dissolved in 660 mL of $CH_2Cl_2$. The solution was cooled to 0° C. and 35.42 g (143.66 mmol) of m-chloroperbenzoic acid was added. The mixture was stirred for 3 h at room temperature and poured into $CHCl_3$. It was then washed with saturated $NaHCO_3$ solution, dried over $MgSO_4$ and the solvent was removed, yielding a crude product that was purified by chromatography on silica gel, using MeOH/EtOAc/hexane mixtures of increasing polarity as eluent. The title compound of the example was obtained as a white solid (17.84 g, 80%).

$^1$H-NMR (300 MHz, $CDCl_3$ δ TMS): 2.68 (s, 3 H), 4.02 (s, 2 H), 6.75 (d, J=8.7 Hz, 2 H), 7.45 (d, J=8.7 Hz, 2 H).

Reference Example 3

4-Isopropoxybenzaldehyde

To a solution of 2 g (16.38 mmol) of 4-hydroxybenzaldehyde in 100 mL of DMF, 2.72 g (19.69 mmol) of $K_2CO_3$, 2.74 g (16.52 mmol) of KI and 3.94 mL (39.38 mmol) of 2-iodopropane was added under argon. The mixture was stirred at 80° C. overnight, concentrated and the residue obtained was partitioned between $CHCl_3$ and $H_2O$. The phases were separated, the aqueous phase was extracted with $CHCl_3$ and the combined organic phases were dried over $MgSO_4$ and concentrated. The crude product obtained was purified by chromatography on silica gel using EtOAc/hexane mixtures of increasing polarity as eluent, to give 2.08 g of the title compound of the example as an oil (77% yield).

$^1$H-NMR (300 MHz, $CDCl_3$ δ TMS): 1.39 (d, J=6 Hz, 6 H), 4.67 (m, 1 H), 6.96 (d, J=8.7 Hz, 2 H), 7.81 (d, J=8.7 Hz, 2 H), 9.87 (s, 1 H).

Reference Example 4

3-Chloro-4-methoxybenzaldehyde

Following a similar procedure to that described in reference example 3, but starting from 3-chloro-4-hydroxybenzaldehyde instead of 4-hydroxybenzaldehyde and using methyl iodide instead of 2-iodopropane, the title compound of the example was obtained as an oil (97% yield).

$^1$H-NMR (300 MHz, $CD_3OD$ δ TMS): 3.98 (s, 3 H), 7.04 (d, J=8.4 Hz, 1 H), 7.77 (d, J=8.4 Hz, 1 H), 7.89 (s, 1 H), 9.84 (s, 1 H).

Reference Example 5

3-Chloro-4-ethoxybenzaldehyde

Following a similar procedure to that described in reference example 3, but starting from 3-chloro-4-hydroxybenzaldehyde instead of 4-hydroxybenzaldehyde and using ethyl iodide instead of 2-iodopropane, the title compound of the example was obtained as an oil (98% yield).

$^1$H-NMR (300 MHz, $CDCl_3$ δ TMS): 1.52 (t, J=6.9 Hz, 3 H), 4.21 (q, J=6.9 Hz, 2 H), 7.02 (d, J=8.7 Hz, 1H), 7.76 (d, J=8.7 Hz, 1 H), 7.91 (s, 1 H), 9.85 (s, 1 H.

Reference Example 6

4-Ethoxy-3-fluorobenzaldehyde

Following a similar procedure to that described in reference example 3, but starting from 3-fluoro-4-hydroxybenzaldehyde instead of 4-hydroxybenzaldehyde and using ethyl iodide instead of 2-iodopropane, the title compound of the example was obtained as an oil (48% yield).

$^1$H-NMR (300 MHz, $CDCl_3$ δ TMS): 1.51 (t, J=7.2 Hz, 3 H), 4.21 (q, J=7.2 Hz, 2 H), 7.06 (t, J=7.8 Hz, 1 H), 7.62 (m, 2 H), 9.86 (s, 1 H).

Reference Example 7

3,4-(Methylenedioxy)benzaldehyde a) Ethyl 3,4-(methylenedioxy)benzoate

A mixture of 3 g (18 mmol) of piperonylic acid and 9 mL of $SOCl_2$ was heated at reflux under argon for 1 h. The solvent was removed and the residue was stirred with a mixture of 5 mL of $Et_3N$ and 75 mL of ethanol for 1.5 h at room temperature. The solvent was removed and the residue was partitioned between $CH_2Cl_2$ and $H_2O$. The layers were separated and the aqueous phase was extracted with $CH_2Cl_2$. The combined organic phases were dried over $MgSO_4$ and concentrated, affording 2.54 g of a crude product that was directly used in the following step.

$^1$H-NMR (300 MHz, $CDCl_3$ δ TMS): 1.36 (t, J=7.2 Hz, 3 H), 4.33 (q, J=7.2 Hz, 2 H), 6.01 (s, 2H), 6.82 (d, J=8.1 Hz, 1 H), 7.46 (s, 1 H), 7.64 (d, J=8.1 Hz, 1 H).

b) 3,4-(Methylenedioxy)phenylmethanol

To a mixture of 0.99 g (26.16 mmol) of $LiAlH_4$ and 80 mL of $Et_2O$, 2.54 g (13.08 mmol) of ethyl 3,4-(methylenedioxy) benzoate (obtained in the preceding section) dissolved in 160 mL of $Et_2O$ was added under argon, and the mixture was stirred overnight at room temperature. A mixture of 1.62 mL of $H_2O$ and 3.41 mL of THF, followed by 1.62 mL of 15% NaOH and then 4.43 mL of $H_2O$ were added dropwise. The resulting mixture was filtered, washed with $Et_2O$ and EtOAc, and the solvent was evaporated. The residue was partitioned between $H_2O$ and EtOAc, the layers were separated, the aqueous phase was extracted with EtOAc and the combined organic phases were dried over $MgSO_4$ and concentrated, yielding 1.88 g of the desired product (94% yield).

$^1$H-NMR (300 MHz, $CDCl_3$ δ TMS): 1.81 (s, 1 H), 4.57 (s, 2 H), 5.96 (s, 2 H), 6.80 (m, 2 H), 6.87 (s, 1 H).

c) Title Compound

To a mixture of 1.18 mL (13.50 mmol) of oxalyl chloride and 17.2 mL of $CH_2Cl_2$, cooled to −78° C., a mixture of 2.1 mL of DMSO and 3.9 mL of $CH_2Cl_2$ was added dropwise and under argon, and the resulting mixture was stirred for 5 min. Next, 1.88 g (12.36 mmol) of 3,4-(methylenedioxy) phenylmethanol (obtained in the preceding section) dissolved in a mixture of 1.6 mL of DMSO and 1.6 mL of $CH_2Cl_2$ was added dropwise and the mixture was stirred for 30 min at −78° C. Then, 14.7 mL (106 mmol) of $Et_3N$ was added, the mixture was stirred for 10 min at the same temperature and was then allowed to warm up to room temperature. It was poured into a mixture of ice and H₂O, extracted with CH$_2$Cl$_2$ and the combined organic phases were dried over MgSO$_4$ and concentrated, yielding 1.6 g of the title compound of the example as an oil (86% yield).

$^1$H-NMR (300 MHz, CDCl$_3$ δ TMS): 6.08 (s, 2 H), 6.93 (d, J=7.8 Hz, 1 H), 7.34 (s, 1 H), 7.42 (d, J=7.8 Hz, 1 H), 9.81 (s, 1 H).

Reference Example 8

3,5-Dichloro-4-methoxybenzaldehyde a) 2,6-Dichloro-4-hydroxymethylphenol

Following a similar procedure to that described in section b of reference example 7, but starting from ethyl 3,5-dichloro-4-hydroxybenzoate instead of ethyl 3,4-(methylenedioxy)benzoate, the desired compound was obtained in a 67% yield.

$^1$H-NMR (300 MHz, CDCl$_3$+CD$_3$OD δ TMS): 3.86 (s, 2 H), 4.54 (s, 2 H), 7.27 (s, 2 H).

b) 3,5-Dichloro-4-methoxyphenylmethanol

Following a similar procedure to that described in reference example 3, but starting from 2,6-dichloro-4-hydroxymethylphenol (obtained in the preceding section) instead of 4-hydroxybenzaldehyde and using methyl iodide instead of 2-iodopropane, the desired compound was obtained in a 77% yield.

$^1$H-NMR (300 MHz, CDCl$_3$ δ TMS): 2.7 (s, broad signal, 1 H), 3.86 (s, 3 H), 4.57 (s, 2 H), 7.26 (s, 2 H).

c) Title Compound

Following a similar procedure to that described in section c of reference example 7, but using 3,5-dichloro-4-methoxyphenylmethanol (obtained in the preceding section) instead of 3,4-(methylenedioxy)phenylmethanol, the title compound of the example was obtained as an oil (94% yield).

$^1$H-NMR (300 MHz, CDCl$_3$ δ TMS): 3.99 (s, 3 H), 7.82 (s, 2 H), 9.86 (s, 1 H).

Reference Example 9

4-Propylbenzaldehyde

Following a similar procedure to that described in reference example 7, but starting from 4-propylbenzoic acid instead of piperonylic acid, the title compound of the example was obtained as an oil.

$^1$H-NMR (300 MHz, CDCl$_3$ δ TMS): 0.98 (t, J=7 Hz, 3 H), 1.68 (m, 2 H), 2.67 (t, J=7 Hz, 2 H), 7.34 (d, J=8.4 Hz, 2 H), 7.80 (d, J=8.4 Hz, 2 H), 9.98 (s, 1 H).

EXAMPLE 1

4-Chloro-5-(4-isopropoxyphenyl)-1-(4-methylsulfonylphenyl)imidazole a) N-(4-Isopropoxybenzyliden)-4-methylsulfonylaniline A mixture of 1.04 g (6.09 mmol) of 4-methylsulfonylaniline (obtained in reference example 1), 1.00 mL (6.09 mmol) of 4-isopropoxybenzaldehyde (obtained in reference example 3) and 25 mL of toluene was heated at reflux in a Dean-Stark for 2 days. The solvent was removed and the crude product obtained was directly used in the next reaction.

$^1$H-NMR (300 MHz, CDCl$_3$ δ TMS): 1.37 (d, J=6.0 Hz, 6 H), 3.07 (s, 3 H), 4.67 (m, 1 H), 6.97 (d, J=8.7 Hz, 2 H), 7.28 (d, J=8.7 Hz, 2 H), 7.84 (d, J=8.7 Hz, 2 H), 7.93 (d, J=8.7 Hz, 2 H), 8.32 (s, 1 H).

b) 5-(4-Isopropoxyphenyl)-1-(4-methylsulfonylphenyl)imidazole

A mixture of 6.09 mmol of N-(4-isopropoxybenzyliden)-4-methylsulfonylaniline (obtained in the preceding section), 1.79 g (9.13 mmol) of tosylmethylisocyanide, 1.68 g (12.16 mmol) of K$_2$CO$_3$, 43 mL of MeOH and 18 mL of DME was heated at reflux for 2 h. The solvent was removed and the residue was partitioned between CH$_2$Cl$_2$ and brine and the layers were separated. The aqueous phase was extracted with CH$_2$Cl$_2$ and the combined organic phases were dried over MgSO$_4$ and concentrated. A crude product was obtained, which was washed with Et$_2$O several times to give 1.40 g of the desired product (65% yield).

$^1$H-NMR (300 MHz, CDCl$_3$ δ TMS): 1.34 (d, J=6.0 Hz, 6 H), 3.10 (s, 3 H), 4.54 (m, 1 H), 6.82 (d, J=8.7 Hz, 2 H), 7.03 (d, J=8.7 Hz, 2 H), 7.21 (s, 1 H), 7.38 (d, J=8.7 Hz, 2 H), 7.74 (s, 1 H), 7.98 (d, J=8.7 Hz, 2 H).

c) Title Compound

A mixture of 1.30 g (3.64 mmol) of 5-(4-isopropoxyphenyl)-1-(4-methylsulfonylphenyl)imidazole (obtained in the preceding section), 0.535 g (4.02 mmol) of N-chlorosuccinimide and 25 mL of acetonitrile was heated at reflux overnight. The solvent was removed and the residue was partitioned between CHCl$_3$ and 1N NaOH solution. The layers were separated, the aqueous phase was extracted with CHCl$_3$ and the combined organic phases were dried over MgSO$_4$ and concentrated. The crude product obtained was purified by chromatography on silica gel, using EtOAc/hexane mixtures of increasing polarity as eluent, affording 1.09 g of the title compound of the example as a white solid (77% yield).

$^1$H-NMR (300 MHz, CDCl$_3$ δ TMS): 1.34 (d, J=6.0 Hz, 6 H), 3.08 (s, 3 H), 4.55 (m, 1 H), 6.84 (d, J=8.7 Hz, 2 H), 7.09 (d, J=8.7 Hz, 2 H), 7.33 (d, J=8.7 Hz, 2 H), 7.63 (s, 1 H), 7.96 (d, J=8.7 Hz, 2 H).

EXAMPLE 2

4-Chloro-5-(4-fluoro-3-methoxyphenyl)-1-(4-methylsulfonylphenyl)imidazole

Following a similar procedure to that described in example 1, but using 4-fluoro-3-methoxybenzaldehyde instead of 4-isopropoxybenzaldehyde, the title compound of the example was obtained as a white solid.

$^1$H-NMR (300 MHz, CDCl$_3$ δ TMS): 3.08 (s, 3 H), 3.77 (s, 3 H), 6.62 (m, 1 H), 6.88 (d, J=8.1 Hz, 1 H), 7.01 (t, J=8.1 Hz, 1 H), 7.34, (d, J=8.7 Hz, 2 H), 7.66 (s, 1 H), 7.99 (d, J=8.7 Hz, 2 H).

EXAMPLE 3

4-Chloro-5-(4-ethoxy-3-fluorophenyl)-1-(4-methylsulfonylphenyl)imidazole

Following a similar procedure to that described in example 1, but using 4-ethoxy-3-fluorobenzaldehyde (obtained in reference example 6) instead of 4-isopropoxybenzaldehyde, the title compound of the example was obtained as a white solid.

$^1$H-NMR (300 MHz, CDCl$_3$ δ TMS): 1.47 (t, J=7.2 Hz, 3 H), 3.09 (s, 3 H), 4.12 (q, J=7.2 Hz, 2 H), 6.92 (m, 3 H), 7.33 (d, J=8.7 Hz, 2 H), 7.64 (s, 1H), 7.99 (d, J=8.7 Hz, 2 H).

EXAMPLE 4

4-Chloro-5-(3,5-difluorophenyl)-1-(4-methylsulfonylphenyl)imidazole

Following a similar procedure to that described in example 1, but using 3,5-difluorobenzaldehyde instead of 4-isopropoxybenzaldehyde, the title compound of the example was obtained as a white solid.

$^1$H-NMR (300 MHz, CDCl$_3$ δ TMS): 3.11 (s, 3 H), 6.74 (d, J=7.8 Hz, 2 H), 6.81 (t, J=8.7 Hz, 1 H), 7.35 (d, J=8.7 Hz, 2 H), 7.68 (s, 1 H), 8.03 (d, J=8.7 Hz, 2 H

EXAMPLE 5

4-Chloro-5-(3-chloro-4-methoxyphenyl)-1-(4-methylsulfonylphenyl)imidazole

Following a similar procedure to that described in example 1, but using 3-chloro-4-methoxybenzaldehyde (obtained in reference example 4) instead of 4-isopropoxybenzaldehyde, the title compound of the example was obtained as a creamy solid.

$^1$H-NMR (300 MHz, CDCl$_3$ δ TMS): 3.09 (s, 3 H), 3.92 (s, 3 H), 6.89 (d, J=8.7 Hz, 1 H), 7.00 (d, J=8.7 Hz, 1 H), 7.27 (s, 1 H), 7.33 (d, J=8.7 Hz, 2 H), 7.65 (s, 1 H), 8.00 (d, J=8.7 Hz, 2 H).

EXAMPLE 6

4-Chloro-5-(3-chloro-4-ethoxyphenyl)-1-(4-methylsulfonylphenyl)imidazole

Following a similar procedure to that described in example 1, but using 3-chloro-4-ethoxybenzaldehyde (obtained in reference example 5) instead of 4-isopropoxybenzaldehyde, the title compound of the example was obtained as a white solid.

$^1$H-NMR (300 MHz, CDCl$_3$ δ TMS): 1.48 (t, J=6.9 Hz, 3 H), 3.09 (s, 3 H), 4.12 (q, J=6.9 Hz, 2 H), 6.87 (d, J=8.4 Hz, 1 H), 6.98 (d, J=8.4 Hz, 1 H), 7.24 (s, 1 H), 7.33 (d, J=8.7 Hz, 2 H), 7.64 (s, 1 H), 7.99 (d, J=8.7 Hz, 2 H).

EXAMPLE 7

4-Chloro-5-[3,4-(methylenedioxy)phenyl]-1-(4-methylsulfonylphenyl)imidazole

Following a similar procedure to that described in example 1, but using 3,4-(methylenedioxy)benzaldehyde (obtained in reference example 7) instead of 4-isopropoxybenzaldehyde, the title compound of the example was obtained as a white solid.

$^1$H-NMR (300 MHz, CDCl$_3$ δ TMS): 3.09 (s, 3 H), 6.01 (s, 2 H), 6.66 (m, 2 H), 6.80 (d, J=7.2 Hz, 1 H), 7.34 (d, J=8.4 Hz, 2 H), 7.63 (s, 1H), 7.99 (d, J=8.4 Hz, 2 H).

EXAMPLE 8

4-Chloro-5-(3,5-dichloro-4-methoxyphenyl)-1-(4-methylsulfonylphenyl)imidazole Following a similar procedure to that described in example 1, but using 3,5-dichloro-4-methoxybenzaldehyde (obtained in reference example 8) instead of 4-isopropoxybenzaldehyde, the title compound of the example was obtained as a creamy solid.

$^1$H-NMR (300 MHz, CDCl$_3$ δ TMS): 3.10 (s, 3 H), 3.94 (s, 3 H), 7.13 (s, 2 H), 7.36 (d, J=8.4 Hz, 2 H), 7.67 (s, 1 H), 8.05 (d, J=8.4 Hz, 2 H).

EXAMPLE 9

4-Chloro-5-(4-isopropylphenyl)-1-(4-methylsulfonylphenyl)imidazole

Following a similar procedure to that described in example 1, but using 4-isopropylbenzaldehyde instead of 4-isopropoxybenzaldehyde, the title compound of the example was obtained as a white solid.

$^1$H-NMR (300 MHz, CDCl$_3$ δ TMS): 1.25 (d, J=6.9 Hz, 6 H), 2.91 (m, 1 H), 3.09 (s, 3 H), 7.11 (d, J=8.1 Hz, 2 H), 7.21 (d, J=8.1 Hz, 2 H), 7.33 (d, J=8.7 Hz, 2 H), 7.64 (s, 1 H), 7.97 (d, J=8.7 Hz, 2 H).

EXAMPLE 10

4-Chloro-5-(4-N,N-diethylaminophenyl)-1-(4-methylsulfonylphenyl)imidazole a) 4-Chloro-1-(4-methylsulfonylphenyl)-5-(4-nitrophenyl)imidazole Following a similar procedure to that described in example 1, but using 4-nitrobenzaldehyde instead of 4-isopropoxybenzaldehyde, the desired compound was obtained as a yellow solid.

$^1$H-NMR (300 MHz, CDCl$_3$ δ TMS): 3.09 (s, 3 H), 7.34 (d, J=8.5 Hz, 2 H), 7.39 (d, J=8.5 Hz, 2 H), 7.72 (s, 1 H), 8.02 (d, J=8.5 Hz, 2 H), 8.20 (d, J=8.5 Hz, 2 H).

b) 5-(4-Aminophenyl)-4-chloro-1-(4-methylsulfonylphenyl)imidazole

A mixture of 1.14 g (3 mmol) of 4-chloro-1-(4-methylsulfonylphenyl)-5-(4-nitrophenyl)imidazole (obtained in the preceding section), 2.88 g (15 mmol) of SnCl$_2$ and 21 mL of ETOH was heated at reflux for 1.5 h. The solvent was removed and the residue was basified with 25% NaOH and extracted with CHCl$_3$. The organic phase was dried over MgSO$_4$ and concentrated. The residue was purified by chromatography on silica gel using hexane/EtOAc mixtures of increasing polarity as eluent, yielding 0.855 g of the product as a yellow solid (81% yield).

$^1$H-NMR (300 MHz, CDCl$_3$+CD$_3$OD δ TMS): 3.08 (s, 3 H), 4.0 (s, 2 H+H$_2$O), 6.60 (d, J=8.5 Hz, 2 H), 6.90 (d, J=8.5 Hz, 2 H), 7.35 (d, J=8.5 Hz, 2 H), 7.66 (s, 1 H), 7.93 (d, J=8.5 Hz, 2 H).

c) Title Compound

To a mixture of 0.69 mL of 3M H$_2$SO$_4$, 0.288 mL (5.15 mmol) of acetaldehyde and 0.432 mL of H$_2$O, cooled to −10° C., 0.3 g (0.86 mmol) of 5-(4-aminophenyl)-4-chloro-1-(4-methylsulfonylphenyl)imidazole (obtained in the preceding section), 0.234 g (6.02 mmol) of NaBH$_4$ and 6.02 mL of THF was slowly added while monitoring that the temperature did not rise above 20° C. Next, solid NaOH was added, the suspension was decanted, washed with H$_2$O and the aqueous phases were extracted with Et$_2$O and EtOAc. The combined organic phases were dried over MgSO$_4$ and concentrated. The crude product obtained was purified by chromatography on silica gel, using EtOAc/hexane mixtures of increasing polarity as eluent, followed by recrystallization from EtOAc and hexane to give 80 mg of the title compound of the example as a white solid (23% yield).

$^1$H-NMR (300 MHz, CDCl$_3$ δ TMS): 1.17 (t, J=7.2 Hz, 6 H), 3.09 (s, 3 H), 3.36 (q, J=7.2 Hz, 4 H), 6.59 (m, 2 H), 6.99 (m, 2 H), 7.36 (d, J=8.4 Hz, 2 H), 7.60 (s, 1 H), 7.97 (d, J=8.4 Hz, 2 H).

EXAMPLE 11

4-[4-Chloro-5-(4-fluoro-3-methoxyphenyl)imidazol-1-yl]benzenesulfonamide a) N-(4-Fluoro-3-methoxybenzyliden)-4-methylsulfinylaniline Following a similar procedure to that described in section a of example 1, but starting from 4-methylsulfinylaniline (obtained in reference example 2) instead of 4-methylsulfonylaniline and from 4-fluoro-3-methoxybenzaldehyde instead of 4-isopropoxybenzaldehyde, the desired compound was obtained, which was directly used in the next step.

$^1$H-NMR (300 MHz, CDCl$_3$ δ TMS): 2.75 (s, 3 H), 3.96 (s, 3 H), 7.20 (m, 3 H), 7.32 (d, J=8.7 Hz, 2 H), 7.69 (d, J=8.7 Hz, 2 H), 8.37 (s, 1 H).

b) 5-(4-Fluoro-3-methoxyphenyl)-1-(4-methylsulfinylphenyl)imidazole

Following a similar procedure to that described in section b of example 1, but starting from N-(4-fluoro-3-methoxybenzyliden)-4-methylsulfinylaniline (obtained in the preceding section) instead of N-(4-isopropoxybenzyliden)-4-methylsulfonylaniline, the desired compound was obtained in 79% yield.

$^1$H-NMR (300 MHz, CDCl$_3$ δ TMS): 3.09 (s, 3 H), 3.74 (s, 3 H), 6.60 (m, 1 H), 6.75 (d, J=8.1 Hz, 1 H), 7.00 (t, J=8.4 Hz, 1 H), 7.27 (s, 1 H), 7.38 (d, J=8.7 Hz, 2 H), 7.98 (s, 1 H), 8.00 (d, J=8.7 Hz, 2 H).

c) 1-[4-(Acetoxymethylsulfanyl)phenyl]-5-(4-fluoro-3-methoxyphenyl)-imidazole 4.2 g (12.71 mmol) of 5-(4-fluoro-3-methoxyphenyl)-1-(4-methylsulfinylphenyl)imidazole (obtained in the preceding section), 38.2 mL of Ac$_2$O and 3.92 g (47.73 mmol) of NaOAc was placed in a flask under argon, and the mixture was heated at reflux overnight. The solvent was removed and the crude product was purified by chromatography on silica gel using EtOAc/hexane mixtures of increasing polarity as eluent, yielding 4.11 g of the desired product (87% yield).

$^1$H-NMR (300 MHz, CDCl$_3$ δ TMS): 2.11 (s, 3 H), 3.70 (s, 3 H), 5.43 (s, 2 H), 6.68 (m, 2 H), 6.98 (t, J=8.4 Hz, 1 H), 7.14 (d, J=8.7 Hz, 2 H), 7.25 (s, 1 H), 7.48 (d, J=8.7 Hz, 2 H), 7.74 (s, 1 H).

d) 1-[4-(Acetoxymethylsulfanyl)phenyl]-4-chloro-5-(4-fluoro-3-methoxyphenyl)imidazole Following a similar procedure to that described in section c of example 1, but starting from 1-[4-(acetoxymethylsulfanyl)phenyl]-5-(4-fluoro-3-methoxyphenyl)imidazole (obtained in the preceding section) instead of 5-(4-isopropoxyphenyl)-1-(4-methylsulfonylphenyl)imidazole, the desired compound was obtained in 53% yield.

$^1$H-NMR (300 MHz, CDCl$_3$ δ TMS): 2.11 (s, 3 H), 3.73 (s, 3 H), 5.42 (s, 2 H), 6.71 (m, 1 H), 6.82 (d, J=8.1 Hz, 1 H), 7.02 (t, J=8.4 Hz, 1 H), 7.09 (d, J=8.7 Hz, 2 H), 7.46 (d, J=8.7 Hz, 2 H), 7.59 (s, 1 H).

e) Sodium 4-[4-chloro-5-(4-fluoro-3-methoxyphenyl) imidazol-1-yl]benzenesulfinate 2.4 g (5.9 mmol) of 1-[4-(acetoxymethylsulfanyl)phenyl]-4-chloro-5-(4-fluoro-3-methoxyphenyl)imidazole (obtained in the preceding section), 18.8 mL of CH$_2$Cl$_2$ and 9.2 mL of MeOH was placed in a flask under argon, and the mixture was cooled to 0° C. Next, 3.83 g (6.19 mmol) of magnesium monoperoxyphtalate hexahydrate was added and the mixture was stirred overnight at room temperature. 83 mL of a 50% mixture of saturated NaHCO$_3$ solution and H$_2$O was added, the layers were separated and the aqueous phase was extracted with CH$_2$Cl$_2$. The organic phases were combined, the solvent was removed and the residue was dissolved in a mixture of 18.8 mL of THF and 9.2 mL of MeOH and was cooled to 0° C. 5.9 mL of 1 N NaOH was added and the mixture was stirred for 1 h at room temperature and was then concentrated by removing H$_2$O by azeotropic distillation with 50% EtOH/toluene mixtures. The residue was dried in vacuo, toluene was added and the mixture was concentrated to dryness, yielding 2.29 g of crude product, which was directly used in the next step.

$^1$H-NMR (300 MHz, CDCl$_3$+CD$_3$OD δ TMS): 3.67 (s, 3 H), 6.70 (m, 1 H), 6.77 (d, J=8.1 Hz, 1 H), 6.96 (t, J=8.4 Hz, 1 H), 7.19 (d, J=8.7 Hz, 2 H), 7.48 (s, 1 H), 7.69 (d, J=8.7 Hz, 2 H).

f) Title Compound

The crude product obtained in the preceding section (5.9 mmol), 29.7 mL of H$_2$O, 0.533 g (6.5 mmol) of NaOAc and 0.734 g (6.5 mmol) of hydroxylamino-O-sulfonic acid were placed in a flask and the mixture was stirred for two nights at room temperature. The resulting mixture was poured into EtOAc, the layers were separated and the aqueous phase was extracted with EtOAc. The combined organic phases were washed with brine, filtered, dried over MgSO$_4$ and concentrated. The residue was purified by chromatography on silica gel using acetone as eluent, yielding 1.249 g of the title compound of the example as a white solid (56% yield).

$^1$H-NMR (300 MHz, CDCl$_3$+CD$_3$OD δ TMS): 3.59 (s, 3 H), 6.55 (m, 1 H), 6.69 (d, J=8.1 Hz, 1 H), 6.87 (t, J=8.4 Hz, 1 H), 7.14 (d, J=8.7 Hz, 2 H), 7.59 (s, 1 H), 7.81 (d, J=8.7 Hz, 2 H).

EXAMPLE 12

4-[4-Chloro-5-(4-ethoxy-3-fluorophenyl)imidazol-1-yl]benzenesulfonamide

Following a similar procedure to that described in example 11, but using 4-ethoxy-3-fluorobenzaldehyde (obtained in reference example 6) instead of 4-fluoro-3-methoxybenzaldehyde, the title compound of the example was obtained as a white solid.

$^1$H-NMR (300 MHz, CDCl$_3$+CD$_3$OD δ TMS): 1.46 (t, J=6.9 Hz, 3 H), 4.13 (q, J=6.9 Hz, 2 H), 6.94 (m, 3 H), 7.31 (d, J=8.4 Hz, 2 H), 7.74 (s, 1 H), 7.97 (d, J=8.4 Hz, 2 H).

EXAMPLE 13

4-[4-Chloro-5-(3-chloro-4-ethoxyphenyl)imidazol-1-yl]benzenesulfonamide

Following a similar procedure to that described in example 11, but using 3-chloro-4-ethoxybenzaldehyde (obtained in reference example 5) instead of 4-fluoro-3-methoxybenzaldehyde, the title compound of the example was obtained as a white solid.

$^1$H-NMR (300 MHz, DMSO δ TMS): 1.32 (t, J=6.9 Hz, 3 H), 4.10 (q, J=6.9 Hz, 2 H), 7.09 (m, 2 H), 7.31 (s, 1 H), 7.43 (s, 2 H), 7.47 (d, J=8.7 Hz, 2 H), 7.84 (d, J=8.7 Hz, 2 H), 8.09 (s, 1 H).

EXAMPLE 14

4-[4-Chloro-5-(3-chloro-4-methoxyphenyl)imidazol-1-yl]benzenesulfonamide

Following a similar procedure to that described in example 11, but using 3-chloro-4-methoxybenzaldehyde (obtained in reference example 4) instead of 4-fluoro-3-methoxybenzaldehyde, the title compound of the example was obtained as a white solid.

$^1$H-NMR (300 MHz, CDCl$_3$+CD$_3$OD δ TMS): 3.87 (s, 3 H), 6.88 (d, J=8.4 Hz, 1H), 6.98 (d, J=8.4 Hz, 1 H), 7.24 (s, 1 H), 7.26 (d, J=8.7 Hz, 2 H), 7.68 (s, 1 H), 7.93 (d, J=8.7 Hz, 2 H).

EXAMPLE 15

4-[4-Chloro-5-(3,5-dichloro-4-methoxyphenyl) imidazol-1-yl]benzenesulfonamide Hydrochloride Following a similar procedure to that described in example 11, but using 3,5-dichloro-4-methoxybenzaldehyde (obtained in reference example 8) instead of 4-fluoro-3- methoxybenzaldehyde, and in the last step carrying out the extraction from the aqueous phase after acidification with hydrochloric acid, the title compound of the example was obtained as a white solid.

$^1$H-NMR (300 MHz, CDCl$_3$+CD$_3$OD δ TMS): 3.92 (s, 3 H), 7.31 (s, 2 H), 7.49 (d, J=8.4 Hz, 2 H), 8.0 (m, 3 H).

EXAMPLE 16

4-Chloro-1-(4-methylsulfonylphenyl)-5-(4-propylphenyl)imidazole

Following a similar procedure to that described in example 1, but using 4-propylbenzaldehyde (obtained in reference example 9) instead of 4-isopropoxybenzaldehyde, the title compound of the example was obtained as a white solid.

$^1$H-NMR (300 MHz, CDCl$_3$ δ TMS): 0.95 (t, J=7.5 Hz, 3 H), 1.63 (m, 2 H), 2.59 (t, J=7.5 Hz, 2 H), 3.08 (s, 3 H), 7.09 (d, J=8.1 Hz, 2 H), 7.15 (d, J=8.1 Hz, 2 H), 7.32 (d, J=8.4 Hz, 2 H), 7.65 (s, 1 H), 7.96 (d, J=8.4 Hz, 2 H).

What is claimed is:

1. A compound of general formula I

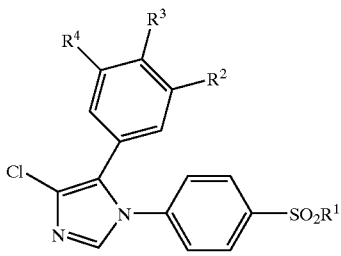

I wherein R$^1$, R$^2$, R$^3$ and R$^4$ represent the specific combinations of values defined in the following table:

| R$^1$ | R$^2$ | R$^3$ | R$^4$ |
|---|---|---|---|
| —CH$_3$ | —H | —OCH(CH$_3$)$_2$ | —H |
| —CH$_3$ | —OCH$_3$ | —F | —H |
| —CH$_3$ | —F | —OCH$_2$CH$_3$ | —H |
| —CH$_3$ | —F | —H | —F |
| —CH$_3$ | —Cl | —OCH$_3$ | —H |
| —CH$_3$ | —Cl | —OCH$_2$CH$_3$ | —H |
| —CH$_3$ | —OCH$_2$O— | | —H |
| —CH$_3$ | —Cl | —OCH$_3$ | —Cl |
| —CH$_3$ | —H | —CH(CH$_3$)$_2$ | —H |
| —CH$_3$ | —H | —N(CH$_2$CH$_3$)$_2$ | —H |
| —NH$_2$ | —OCH$_3$ | —F | —H |
| —NH$_2$ | —F | —OCH$_2$CH$_3$ | —H |
| —NH$_2$ | —Cl | —OCH$_2$CH$_3$ | —H |
| —NH$_2$ | —Cl | —OCH$_3$ | —H |
| —NH$_2$ | —Cl | —OCH$_3$ | —Cl |
| —CH$_3$ | —H | —CH$_2$CH$_2$CH$_3$ | —H | and the salts, solvates and prodrugs thereof.

2. A compound according to claim 1 which is 4-chloro-5-(4-isopropoxyphenyl)-1-(4-methylsulfonylphenyl) imidazole or a salt, solvate or prodrug thereof.

3. A compound according to claim 1 which is 4-chloro-5-(4-fluoro-3-methoxyphenyl)-1-(4-methylsulfonylphenyl) imidazole or a salt, solvate or prodrug thereof.

4. A compound according to claim 1 which is 4-chloro-5-(4-ethoxy-3-fluorophenyl)-1-(4-methylsulfonylphenyl) imidazole or a salt, solvate or prodrug thereof.

5. A compound according to claim 1 which is 4-chloro-5-(3,5-difluorophenyl)-1-(4-methylsulfonylphenyl) imidazole or a salt, solvate or prodrug thereof.

6. A compound according to claim 1 which is 4-chloro-5-(3-chloro-4-methoxyphenyl)-1-(4-methylsulfonylphenyl) imidazole or a salt, solvate or prodrug thereof.

7. A compound according to claim 1 which is 4-chloro-5-(3-chloro-4-ethoxyphenyl)-1-(4-methylsulfonylphenyl) imidazole or a salt, solvate or prodrug thereof.

8. A compound according to claim 1 which is 4-chloro-5-[3,4-(methylenedioxy)phenyl]-1-(4-methylsulfonylphenyl)imidazole or a salt, solvate or prodrug thereof.

9. A compound according to claim 1 which is 4-chloro-5-(3,5-dichloro-4-methoxyphenyl)-1-(4-methylsulfonylphenyl)imidazole or a salt, solvate or prodrug thereof.

10. A compound according to claim 1 which is 4-chloro-5-(4-isopropylphenyl)-1-(4-methylsulfonylphenyl) imidazole or a salt, solvate or prodrug thereof.

11. A compound according to claim 1 which is 4-chloro-5-(4-N,N-diethylaminophenyl)-1-(4-methylsulfonylphenyl) imidazole or a salt, solvate or prodrug thereof.

12. A compound according to claim 1 which is 4-[4-chloro-5-(4-fluoro-3-methoxyphenyl)imidazol-1-yl] benzenesulfonamide or a salt, solvate or prodrug thereof.

13. A compound according to claim 1 which is 4-[4-chloro-5-(4-ethoxy-3-fluorophenyl)imidazol-1-yl] benzenesulfonamide or a salt, solvate or prodrug thereof.

14. A compound according to claim 1 which is 4-[4-chloro-5-(3-chloro-4-ethoxyphenyl)imidazol-1-yl] benzenesulfonamide or a salt, solvate or prodrug thereof.

15. A compound according to claim 1 which is 4-[4-chloro-5-(3-chloro-4-methoxyphenyl)imidazol-1-yl] benzenesulfonamide or a salt, solvate or prodrug thereof.

16. A compound according to claim 1 which is 4-[4-chloro-5-(3,5-dichloro-4-methoxyphenyl)imidazol-1-yl] benzenesulfonamide or a salt, solvate or prodrug thereof.

17. A compound according to claim 1 which is 4-chloro-1-(4-methylsulfonylphenyl)-5-(4-propylphenyl)imidazole or a salt, solvate or prodrug thereof.

18. Process for preparing a compound of formula I according to claim 1 which comprises:

a) reacting a compound of formula II

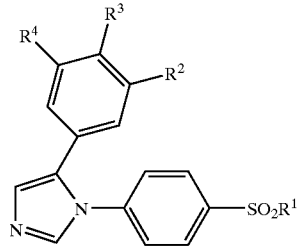

II wherein R$^1$, R$^2$, R$^3$ and R$^4$ have the meaning described in claim 1, with a chlorinating agent; or b) when in a compound of formula I R$^1$ represents —CH$_3$, reacting a compound of formula VI

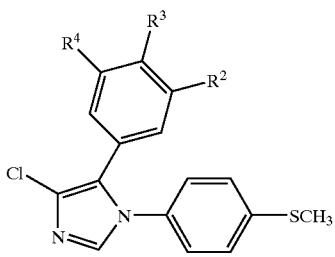

wherein R², R³ and R⁴ have the meaning described in claim 1, with an oxidizing agent; or c) when in a compound of formula I R¹ represents —NH₂, reacting a compound of formula VII

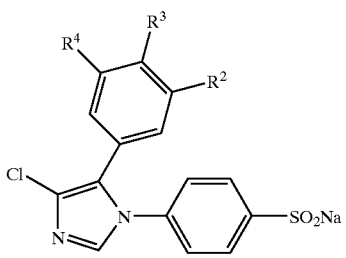

wherein R², R³ and R⁴ have the meaning described in claim 1, with hydroxylamine-O-sulfonic acid; or d) if desired, after the above steps, reacting a compound of formula I with an acid or a base to give the corresponding salt.

19. A pharmaceutical composition which comprises an effective amount of a compound of formula I according to claim 1 or a pharmaceutically acceptable salt, solvate or prodrug thereof and one or more pharmaceutically acceptable excipients.

20. A method of treating a disease mediated by cyclooxygenase which comprises administering to a patient in need thereof a medicament comprising an effective amount of a compound of claim 1 or a pharmaceutically acceptable salt, solvate or prodrug thereof.

21. A method of treating a disease mediated by cyclooxygenase-2 which comprises administering to a patient in need thereof a medicament comprising an effective amount of a compound of claim 1 or a pharmaceutically acceptable salt, solvate or prodrug thereof.

22. A method of treating inflammation, pain or fever which comprises administering to a patient in need thereof a medicament comprising an effective amount of a compound of claim 1 or a pharmaceutically acceptable salt, solvate or prodrug thereof.

23. A method of inhibiting prostanoid-induced smooth muscle contraction which comprises administering to a patient in need thereof a medicament comprising an effective amount of a compound of claim 1 or a pharmaceutically acceptable salt, solvate or prodrug thereof.

24. A method of treating dysmenorrhea, preterm labor, asthma or bronchitis, which comprises administering to a patient in need thereof a medicament comprising an effective amount of a compound of claim 1 or a pharmaceutically acceptable salt, solvate or prodrug thereof.

25. A method of treating familial adenomatous polyposis which comprises administering to a patient in need thereof a medicament comprising an effective amount of a compound of claim 1 or a pharmaceutically acceptable salt, solvate or prodrug thereof.

26. A method of treating cancer which comprises administering to a patient in need thereof a medicament comprising an effective amount of a compound of claim 1 or a pharmaceutically acceptable salt, solvate or prodrug thereof.

27. A method according to claim 26, wherein the cancer is a gastrointestinal cancer.

28. A method according to claim 27, wherein the gastrointestinal cancer is colon cancer.

29. A method of treating cerebral infarction, epilepsy or neurodegenerative disease which comprises administering to a patient in need thereof a medicament comprising an effective amount of a compound of claim 1 or a pharmaceutically acceptable salt, solvate or prodrug thereof.

30. A method according to claim 29, wherein the neurodegenerative disease comprises Alzheimer's disease or dementia.

* * * * *